United States Patent [19]

Trueb

[11] 4,042,370

[45] Aug. 16, 1977

[54] DI-(ACYLOXYALKYL)-β-HALOETHANE-PHOSPHONATES AND DITHIOPHOSPHONATES AND USE AS PLANT GROWTH REGULATORS

[75] Inventor: Werner Trueb, Therwil, Switzerland

[73] Assignee: Sandoz Ltd., Basel, Switzerland

[21] Appl. No.: 612,501

[22] Filed: Sept. 11, 1975

[30] Foreign Application Priority Data

Sept. 18, 1974 Switzerland .................. 12677/74

[51] Int. Cl.² .......................... A01N 9/36; C07F 9/40
[52] U.S. Cl. .................................... 71/86; 71/87;
260/293.51; 260/293.85; 260/326.8;
260/326.82; 260/345.1; 260/347.91; 260/347.2;
260/348.42; 260/456 R; 260/938; 260/456 NS;
260/940; 260/942; 260/946; 260/948; 260/956;
544/157
[58] Field of Search ................ 260/942, 940, 938;
71/86, 87

[56] References Cited

U.S. PATENT DOCUMENTS

| 2,928,861 | 3/1960 | Short ................. 260/942 X |
| 3,196,190 | 7/1965 | Nischk et al. ......... 260/942 X |
| 3,385,688 | 5/1968 | Regel ................. 71/87 X |
| 3,547,878 | 12/1970 | Savides ............... 260/45.8 |
| 3,626,037 | 12/1971 | Randall et al. ........ 71/86 X |
| 3,879,188 | 4/1975 | Fritz et al. .......... 71/86 |

FOREIGN PATENT DOCUMENTS

| 2,050,247 | 5/1971 | Germany ................. 71/86 |
| 2,054,138 | 5/1971 | Germany ................. 71/86 |
| 2,212,604 | 10/1972 | Germany ................. 71/86 |
| 1,194,433 | 6/1970 | United Kingdom ......... 71/86 |
| 1,334,850 | 10/1973 | United Kingdom ......... 71/86 |
| 1,327,905 | 8/1973 | United Kingdom ......... 71/86 |
| 1,320,870 | 6/1973 | United Kingdom ......... 71/86 |

Primary Examiner—Joseph P. Brust
Attorney, Agent, or Firm—Gerald D. Sharkin; Richard E. Vila

[57] ABSTRACT

β-Haloethanephosphonates and thio derivatives thereof of formula,

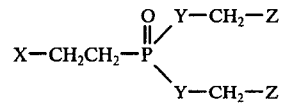

where
X signifies chlorine or bromine,
Y signifies oxygen or sulphur, and
Z signifies a carboxylic acid ester or carbamoyl group, or an optionally further substituted methyl or ethyl group substituted by such a group, or signifies an acylmethyl, optionally aryl-substituted alkenyl or alkynyl, cyclic ether, e.g. tetrahydropyranyl, or optionally mono-substituted cyanomethyl group, or signifies an alkyl-, cycloalkyl- or aryl-thio, -sulphinyl or -sulphonyl group, or an optionally further substituted methyl or ethyl group substituted by such a group, or signifies a sulphonic acid ester group, or an optionally further substituted methyl or ethyl group substituted by such a group, are useful as regulators of plant growth or plant secretion, especially as stimulators of latex flow in latex-forming plants.

14 Claims, No Drawings

Di-(ACYLOXYALKYL)-β-HALOETHANE-PHOSPHONATES AND DITHIOPHOSPHONATES AND USE AS PLANT GROWTH REGULATORS

The present invention relates to β-haloethanephosphonates and their thio derivatives which are useful as plant growth regulating agents.

Accordingly the present invention provides compounds of formula I,

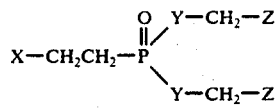

where
X signifies chlorine or bromine,
Y signifies oxygen or sulphur,
and
Z signifies a radical of formula

wherein
R signifies hydrogen, $C_1-C_6$ alkyl, $C_3-C_6$ cycloalkyl, unsubstituted phenyl or phenyl substituted by one or more electron-withdrawing substituents,
$R_1$ signifies $C_1-C_8$ alkyl, $C_3-C_6$ cycloalkyl, unsubstituted phenyl or phenyl substituted by one or more electron-withdrawing substituents, and $n$ signifies 0, 1 or 2, or a radical or formula

wherein
R and $n$ are as defined above, and each of $R_2$ and $R_3$, independently, signifies hydrogen, $C_1-C_6$ alkyl or phenyl,
or
$R_2$ and $R_3$, together with the nitrogen atom to which each is attached, forms a heterocyclic ring of up to 7 members which optionally includes a second hetero atom selected from oxygen, sulphur and nitrogen, or a radical of formula

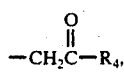

wherein $R_4$ is as defined for $R_1$ above, or a radical of formula $-(CH_2)_m-CR_5 = CHR_6$ or $-(CH_2)_m-C \equiv C-R_7$,
wherein
each of $R_5$, $R_6$ and $R_7$ signifies hydrogen, $C_1-C_8$ alkyl, unsubstituted phenyl or phenyl substituted by one or more electron-withdrawing substituents, and $m$ signifies 0, 1 or 2, or a radical of formula

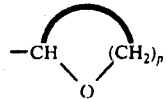

wherein $p$ signifies 1, 2, 3 or 4, or a radical of formula

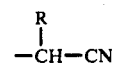

wherein
R is as defined above, or a radical of formula

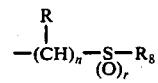

wherein R and $n$ are as defined above, $r$ signifies 0, 1 or 2, and $R_8$ is as defined for $R_1$ above, or a radical of formula

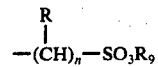

wherein R and $n$ are as defined above, and $R_9$ is as defined for $R_8$ above.

In the above definition, it is to be understood that any alkyl group may be straight or branched chain when containing 3 or more carbon atoms. Preferred examples of electron-withdrawing substituents for any substituted phenyl group are halogen, cyano, carboxy, $C_2-C_8$ alkoxycarbonyl, $C_2-C_8$ alkylcarbamoyl, trihaloalkyl, $C_1-C_8$ alkylsulphinyl unsubstituted phenylsulphinyl, phenylsulphinyl substituted by a methyl or ethyl group, or two methyl groups, $C_1-C_8$ alkylsulphonyl, unsubstituted phenylsulphonyl, phenylsulphonyl substituted by a methyl or ethyl group or two methyl groups, and nitro. By halogen is meant fluorine, chlorine or bromine. Preferred heterocyclic rings signified by $NR_2R_3$ are pyrrolidino, piperidino and morpholino.

Preferably in the compounds of formula I, X is chlorine and, independently, Y is preferably oxygen. Independently from the values of X and Y, Z is preferably a radical of formula

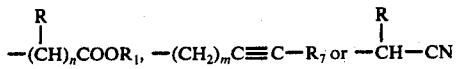

When Z is

$n$ is preferably 0 and, independently, $R_1$ is preferably alkyl. In particular the preferred significance of Z in this case is butoxycarbonyl, more specifically, n-butoxycarbonyl.

When Z is $-(CH_2)_mC \equiv C-R_7$, independently $m$ is preferably 1 and $R_7$ hydrogen. In particular the preferred significance of Z in this case is propargyl.

When

Z is 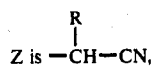

R is preferably hydrogen.

Particularly preferred compounds of formula I are di-(n-butoxycarbonylmethyl) 2-chloroethanephosphonate, di-propargyl 2-chloroethanephosphonate and di-(2-cyanoethyl) 2-chloroethanephosphonate.

The present invention further provides a process for the production of a compound of formula I, as defined above, which comprises reacting a compound of formula II, $$X-CH_2CH_2-\overset{O}{\underset{\|}{P}}(L)_2 \qquad II$$

where
X is as defined above, and L signifies chlorine or bromine, with a compound of formula III, $$MY - CH_2Z \qquad III$$

where Y and Z are as defined above, and M signifies hydrogen or the equivalent of a cation, in such a proportion that both chlorine or bromine atoms signified by $(L)_2$ in the compound of formula II are replaced by $-Y-CH_2-Z$ radicals, and with the proviso that when M is hydrogen, the reaction is effected in the presence of an acid acceptor.

The preferred cations for M are sodium and potassium.

The production is preferably effected by adding the compound of formula III to a stirred solution or suspension of the compound of formula II in a suitable anhydrous solvent or diluent, e.g. a hydrocarbon such as benzene or toluene, a halogenated hydrocarbon such as chloroform or chlorobenzene, a ketone such as acetone or butan-2-one, a nitrile such as acetonitrile, an ester such as an ester of acetic acid, an amide such as dimethyl formamide, or an ether such as dioxan, tetrahydrofuran or diethyl ether, of which ether solvents the latter two are preferred, or in a mixture of solvents, and continuing stirring, for example over a period of up to 3 days, optionally with heating, for example in the range 25° to 40° C. The product may thereafter be isolated by a conventional technique.

When an acid acceptor is used in the reaction medium, this may be a tertiary organic base such as triethylamine, N-methylmorpholine, methyl-di-isopropylamine or pyridine, of which pyridine is preferred.

The reaction is generally exothermic, and appropriate care must be taken in its control.

The compounds of formula II used as intermediates are known, whereas only some of the compounds of formula III are known, the remainder being producible by known methods or analogously to such known methods.

The compounds of the present invention are useful as plant growth regulating agents, in particular plant growth stimulating agents. They are especially useful in stimulating plant secretion, e.g. of latex, plant gums, resins and useful terpenoid constituents.

Of especial interest is the effect of the compounds of the present invention in stimulating latex flow in latex forming plants, e.g. in *Hevea brasiliensis*. The three aforementioned specific compounds are particularly notable in this regard.

Accordingly the present invention further provides a method of regulating the growth of plants or regulating plant secretion by applying to the plants an effective amount of a compound of formula I, as defined above. The method of the invention is especially preferred for stimulating latex flow in latex-forming plants, preferably *Hevea brasiliensis*.

The compounds are generally applied as a formulation in a suitable plant growth regulator carrier, diluent and/or adjuvant in liquid, semi-liquid or solid form, the compound perferably being blended intimately in each case with the appropriate formulation medium, and such formulations are also provided by the present invention. Examples of such formulations are as follows, the percentages being by weight:- a. For di-(n-butoxycarbonylmethyl) 2-chloroethane-phosphonate as the compound of formula I:
  10% compound, 13% xylene and 77% coconut oil blended intimately
  15% compound, 18% xylene and 67% coconut oil blended intimately
  22% compound, 25% xylene and 53% coconut oil blended intimately.

b. For di-propargyl 2-chloroethane -phosphonate as the compound of formula I:
  10% compound, 13% xylene and 77% coconut oil blended intimately
  22% compound, 25% xylene and 53% coconut oil blended intimately.

c. For di-(2-cyanoethyl) 2-chloroethane-phosphonate as the compound of formula I:
  10% compound, 47% cyclohexanone and 43% coconut oil blended intimately.
  15% compound, 51% cyclohexanone and 34% coconut oil blended intimately.
  22% compound, 55% cyclohexanone and 23% coconut oil blended intimately.

The effect of the compounds of the invention in stimulating latex flow in latex forming plants is illustrated in the following test:-

A field trial was conducted on *Hevea brasiliensis* trees (Indian clone 331) of about 15 years old in the state of Karala, India. The period of the test coincided with a normal tapping season. i.e. when rainfall had set in following a seasonal dry period.

On each tree a surface layer of bark, immediately below and parallel with the existing tapping cut, as a strip of the width corresponding to about 8 weeks tapping consumption, was carefully abraded and removed. The penetration was just sufficient to expose but not to pierce the red cambium. To the exposed strip of red cambium 2.5 ml of the 10% formulation of di-(2-cyanoethyl) 2-chloroethane -phosphonate detailed in (a) above was evenly applied with a brush.

During the ensuing approx. 8 weeks period the treated exposed bark strip was removed in equal proportions every 2 – 3 days according to normal tapping practice. The latex produced was collected and its weight measured. Determination of the dry rubber content was also determined by a conventional method, and it was found as a result that there was a 100- to 250-fold increase in yield per tree compared to the yield from untreated trees of the same age and clone which were included in the trial for comparison purposes.

For use in latex flow stimulation the compounds of the invention are preferably applied in a jelly formulation, which consists of the compound of formula I dissolved in an organic solvent, this solution then being thickened by means of a thickening agent until the desired jelly constituency has been achieved. The organic solvent may consist entirely of a single solvent, e.g. an aromatic or aliphatic solvent; or may consist of a mixture of solvents. It is often advantageous to include a polar solvent such as dimethylsulphoxide or dimethylformamide in a mixed solvent to aid dissolution of the compound. An example of a suitable aromatic solvent is xylene, and of a suitable thickening agent is hydroxyethyl cellulose.

In the following example of a suitable jelly formulation for use in stimulating latex flow, the percentages are by weight:

10% of a compound of formula I dissolved in 20% of an aromatic solvent, e.g. xylene, and 67% of a polar solvent, e.g. dimethylsulphoxide or dimethylformamide to which has been added 3% of hydroxyethyl cellulose with vigorous stirring until thickening has developed sufficiently to achieve the desired jelly constituency.

The amount of compound of formula I applied to rubber trees, e.g. *Hevea brasiliensis,* will vary depending on the compound employed, the mode of application, the species and size of tree and the prevailing climatic conditions, amongst other factors. However, satisfactory results are generally obtained when the compound of formula I is applied at the rate of 0.2 to 0.8 g per tree. When applied in a 10% jelly formulation, this corresponds to 2 to 8 g of jelly formulation containing 10% w/w of compound of formula I per tree.

The following Examples illustrate the production of the compounds of the invention. Temperatures are in degrees Centigrade.

EXAMPLE 1: Di(2-cyanoethyl) 2-chloroethane-phosphonate

To a solution of 45.5 g (0.25 mol) of 2-chloroethane phosphonic acid dichloride in 1200 ml of absolute diethyl ether are added 35.5 g (0.5 mol) of 3-hydroxypropionitrile. The solution is observed to become cloudy. At room temperature 35.5 g (0.488 mol) of pyridine are added dropwise, during which the temperature increases to 30° and crystallisation occurs. The mixture is stirred for 60 hours at 35° after which the ethereal solution is decanted.

Subsequently the hydrochloride residue is dissolved in 100 ml of water and the resulting solution is subjected to a fluid extraction with diethyl ether over a period of 3 days. Methylene chloride is then added to effect the solution of the separated oil and the whole is dried over anhydrous sodium sulphate and subsequently evaporated. Finally the residual oil is evaporated in a rotary evaporator for 3 hours at 45°, the product having the following characterisation data:
Analysis: $C_8H_{12}ClN_2O_3P$ Mol weight: 250

| | | | | | |
|---|---|---|---|---|---|
| Calc. | C 38.3% | H 4.8% | Cl 14.1% | N 11.2% | P 12.4% |
| Found | 39.0% | 5.2% | 14.0% | 11.1% | 11.9% |

$n_D = 1.475$ NMR ($\delta$, ppm) in CDCl$_3$: CH$_2$ with P multiplet 2.17 – 2.73; CH$_2$ with Cl: 3.81 (5 lines). Ester-CH$_2$ with CN at 2.82 (triplet) and ester-CH$_2$ with 0 at about 4.36 (multiplet).

EXAMPLE 2: Di-(ethoxycarbonylethyl) 2-chloroethanephosphonate

To a solution of 9.1 g (0.05 mol) of 2-chloroethane phosphonic acid dichloride and 11.5 g (0.098 mol) of 3-hydroxypropionic acid ethylester in 200 ml of absolute diethyl ether are added dropwise with stirring 7.75 g (0.098 mol) of pyridine in 20 ml of absolute diethyl ether at room temperature. During the addition the hydrochloride formed crystallises out and the temperature increases to 35°. Stirring is continued for 60 hours at room temperature.

The hydrochloride salt is collected by filtration and the ethereal filtrate is evaporated. The residue is further dried by rotation under high vacuum at 40° over a period of 3 hours, the product having the following characterisation data: $n_D = 1.459$
Analysis: $C_{12}H_{22}ClO_7P$ Mol weight: 344.7

| | | | | |
|---|---|---|---|---|
| Calc. | C 41.8% | H 6.4% | Cl 10.3% | P 9.0% |
| Found | 41.6% | 6.6% | 10.4% | 10.0% |

NMR ($\delta$, ppm) in CDCl$_3$: CH$_2$ with P as multiplet between 2.05 and about 2.70; CH$_2$ with Cl as multiplet around 3.7. Ester-CH$_2$ with CO at 2.68 (triplet),

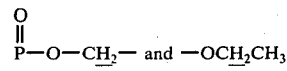

as
multiplet around 4.3.
CH$_3$ of the ethyl group as triplet at 1.28.

EXAMPLE 3: Di-(2-ethoxycarbonyl-2-phenylethyl) 2-chloroethanephosphate

To a solution of 19.4 g (0.1 mol) of 2-phenyl-3-hydroxypropionic acid ethylester and 9.1 g (0.05 mol) of 2-chloroethane phosphonic acid dichloride in 100 ml of absolute diethyl ether are added dropwise with stirring 7.9 g (0.1 mol) of absolute pyridine in 50 ml of absolute diethyl ether at room temperature, during which the temperature increases to 30° and crystallisation occurs. Stirring is continued for 35 hours at 25° after which the crystals are removed by filtration and the ethereal filtrate is washed with water to neutrality, dried and concentrated. The resulting oil further evaporated furtherevaporated in a rotary evaporator at 25° for 2 hours yielding a product with the following characterisation data: Analysis: $C_{24}H_{30}ClO_7P$ Mol weight: 496.5

| | | | | |
|---|---|---|---|---|
| Calc. | C 58.0% | H 6.1% | Cl 7.1% | P 6.2% |
| Found | 57.7% | 6.3% | 7.2% | 5.8% |

NMR ($\delta$, ppm) in CDCl$_3$: ester-CH$_3$ at 1.2 (triplet), ester-CH$_2$ at 4.16 (quartet). CH$_2$ with P as multiplet between 1.8 and 2.55. Remaining aliphatic protons as superimposed multiplets of 3.3 – 4.7.
Aromatic protons: 7.30 (singlet).
$n_D^{20°} = 1.5186$

EXAMPLE 4: Di-(2-ethoxycarbonylethyl) 2-chloroethanedithiophosphonate

To a solution of 9.1 g (0.05 mol) of 2-chloroethane phosphonic acid dichloride and 13.4 g (0.1 mol) of 2-mercaptopropionic acid ethylester in 100 ml of absolute diethyl ether are added 7.9 g (0.1 mol) of absolute pyridine in 50 ml of absolute diethyl ether with stirring. During the reaction white crystals are produced. Stirring is continued for 15 hours at 40°.

To the reaction mixture are then added 100 ml of water, and the aqueous solution is extracted with 5 50 ml amounts of diethyl ether. The ethereal extracts are washed with water to neutrality, dried and concentrated by evaporation.

The resulting colourless oil is dissolved in methylene chloride and the solution is passed down a silica gel column after which the product isolated from the solution is chromatographed with diethyl ether. The product is a yellow oil with the following characterisation data.
Analysis: $C_{12}H_{22}ClO_5PS_2$ Mol weight: 376.5

| | | | | | |
|---|---|---|---|---|---|
| Calc. | C 38.2% | H 5.9% | Cl 9.4% | P 8.2% | S 17.0% |
| Found | 39.3% | 6.2% | 9.2% | 7.9% | 17.5% |

NMR ($\delta$, ppm) in $CDCl_3$: ester-$CH_3$ as triplet at 1.26; $CH_2$ with S and $CH_2$ with CO as partially overlapping multiplets between 2.5 and 3.37. $CH_2$ with Cl between 3.43 and 3.93 (multiplet). Ester-$CH_2$ with 0 as quartet at 4.19 $n_D^{20°}$ = 1.520

EXAMPLE 5:
Di-[2-(N,N-diethylcarbamoyl)ethyl]2-chloroethane-phosphonate

To a solution of 14.5 g (0.1 mol) of N,N-diethyl-3-hydroxypropionamide (produced according to JACS 73, 3168-71 (1951)) and 7.9 g (0.1 mol) of absolute pyridine in 100 ml of tetrahydrofuran are added dropwise 9.1 g (0.05 mol) of 2-chloroethane phosphonic acid dichloride with stirring. During the addition the temperature increases to 40° and thereafter stirring is continued for a further 15 hours at 25° .

The reaction mixture is evaporated and the residue is dissolved in methylene chloride, the solution then being washed with water. After separation of the aqueous phase the latter is extracted 3 times with 50 ml of methylene chloride. The combined methylene chloride extracts are washed with water until the aqueous phase attains a pH of 5 - 6. The methylene chloride solution is dried and then concentrated by evaporation, a yellow oil being produced as a residue. This is subjected to chromatography on neutral aluminium oxide (Woelm: column size 20 × 4 cm) with ethyl acetate, a colourless oil being finally obtained, with the following characterisation data:
Analysis: $C_{16}H_{32}ClN_2O_5P$ Mol weight: 398.5

| | | | | | |
|---|---|---|---|---|---|
| Calc. | C 48.2% | H 8.1% | | N 7.0% | P 7.8% |
| Found | 48.3% | 8.0% | | 6.9% | 7.5% |

NMR ($\delta$, ppm) in $CDCl_3$: amide-$CH_3$ multiplet 0.95 - 1.35; $CH_2$ with P about 2.0 - 2.5. $CH_2$ with CO 2.5 - 2.85; $CH_2$ with N 3.2 - 3.5; $CH_2$ with Cl about 3.4 - 3.9 (partially covered); $CH_2$ with 0 4.0 - 4.55 (all multiplets).

EXAMPLE 6:
Di-[2-(N-n-butylcarbamoyl)ethyl]2-chloroethanephosphonate

To a solution of 14.5 g (0.1 mol) of N-butyl 3-hydroxypropionamide (produced as described in JACS 73, 3168-71 (1951)) and 9.1 g (0.05 mol) of 2-chloroethane phosphonic acid dichloride in 100 ml of absolute tetrahydrofuran are added dropwise 7.9 g (0.1 mol) of absolute pyridine with stirring. Upon the addition the solution begins to boil and an oily precipitate appears. Stirring is continued for a further 60 hours at 25° .

The mixture is evaporated and the oily residue is dissolved in chloroform. This solution is washed with water and the aqueous phase is extracted with 3 50 ml portions of chloroform. The combined chloroform extracts are washed with water until the aqueous phase reaches a pH of 5 and then the chloroform solution is dried and concentrated by evaporation. Produced is a yellow oil, which is subjected to chromatography on silica gel (column size 25 × 3.5 cm) firstly with ethyl acetate and subsequently with methanol, resulting in a yellow oil as the main fraction extracted with methanol. This fraction crystallises on standing and is submitted to recrystallisation with a mixture of methylene chloride and diethyl ether, affording white crystals, m.p. 68° - 72°.Further characterisation data are as follows:
Analysis: $C_{16}H_{32}ClN_2O_5P$ Mol weight: 398.5

| | | | | | |
|---|---|---|---|---|---|
| Calc. | C 48.2% | H 8.1% | Cl 8.9% | N 7.0% | P 7.8% |
| Found | 48.2% | 8.3% | 9.4% | 6.5% | 8.4% |

NMR ($\delta$, ppm) in $CDCl_3$: butyl-$CH_3$ as multiplet around 0.95. The adjacent 4 butyl protons between 1.1 and 1.65 (multiplet). $CH_2$ with P 2.0 - about 2.5. $CH_2$ with CO as triplet at 2.56. $CH_2$ with NH as multiplet between 3.05 and 3.45. $CH_2$ with Cl at 3.55 - 3.95 and $CH_2$ with O at 4.18 - 4.53 (multiplet). NH-protons as broad signal at 6.54.

EXAMPLE 7:
Di-2-ethylthioethyl)2-chloroethanephosphonate

To a solution of 18.1 g (0.1 mol) of 2-chloroethane phosphonic acid dichloride in 150 ml of absolute ether is added dropwise with stirring a solution of 21.2 g (0.2 mol) of hydroxyethyl ethyl sulphide and 15.8 g of absolute pyridine in 100 ml of absolute ether at room temperature, during which the temperature increases to 35° and crystallisation occurs. Stirring is continued for a further 14 hours at 25° after which the crystals are removed by filtration and the ethereal filtrate is washed to neutrality with 5% hydrogen carbonate solution and water. It is dried and evaporated and further dried by rotation under high vacuum for 2 hours. A yellow oil is obtained having the following characterisation data:
Analysis: $C_{10}H_{22}ClO_3PS_2$ Mol weight: 320.8

| | | | | | |
|---|---|---|---|---|---|
| Calc. | C 37.4% | H 6.9% | Cl 11.1% | P 9.7% | S 20.0% |
| Found | 37.4% | 6.7% | 11.6% | 8.8% | 19.5% |

$n_D^{20°}$ = 1.5079
NMR ($\delta$, ppm) in $CDCl_3$: ester-$CH_3$ as triplet at 1.27; $CH_2$ with P at 2.0 - about 2.5 and $CH_2$ with S at 2.4 –3.0 (multiplet). $CH_2$ with Cl between 3.5 and about 3.9 and $CH_2$ with O at 4.0 - 4.4 (multiplet). $n_D^{200}$ . 1.5079

EXAMPLE 8: Di-allyl 2-chloroethanephosphonate

To a solution of 11.6 g (0.2 mol) of allyl alcohol and 18.1 g (0.1 mol) of 2-chloroethane phosphonic acid dichloride in 150 ml of absolute ether are added dropwise with stirring 15.8 g (0.2 mol) of pyridine. When the exothermic reaction is complete, stirring is continued for 15 hours at 40° after which the precipitated hydrochloride is removed by filtration and the ethereal filtrate washed to neutrality with water, dried and then evaporated. It is further dried by rotation under high vacuum over a period of 2 hours at 25°.A yellowish oil is obtained having the following characterisation data: Analysis: $C_8H_{14}ClO_3P$ Mol weight: 224.6

| | | | | |
|---|---|---|---|---|
| Calc. | C 42.7% | H 6.3% | Cl 15.9% | P 13.9% |
| Found | 42.3% | 6.5% | 17.9% | 14.2% |

$n_D^{20°}$ = 1.4662 NMR ($\delta$, ppm) in $CDCl_3$: $CH_2$ with P as multiplet at 2.0 - 2.6; $CH_2$ with Cl as multiplet at 3.5 - 4.0. Allyl protons as multiplets about 4.5. Resultant vinyl protons 5.1 - 5.5 and vinyl protons with $CH_2$ between 5.6 and 6.2 (multiplet).

EXAMPLE 9: Di-propargyl 2-chloroethanephosphonate

To a solution of 11.9 g (0.2 mol) of propargyl alcohol and 18.1 g (0.1 mol) of 2-chloroethane phosphonic acid dichloride in 150 ml of absolute diethyl ether are added with stirring 15.8 g (0.2 mol) of absolute pyridine, whereupon an exothermic reaction occurs. Stirring is continued for a further 15 hours at 40°.

The precipitated hydrochloride is removed from the reaction mixture by filtration, and the ethereal filtrate is washed to neutrality with water, dried and evaporated. After further drying of the residue under high vacuum for 2 hours at 25° a yellow oil is obtained as the product having the following characterisation data: $n_D^{20°}$ = 1.4839 Analysis: $C_8H_{10}ClO_3P$ Mol weight: 220.6

|  |  |  |  |  |
|---|---|---|---|---|
| Calc. | C 43.6% | H 4.5% | Cl 16.1% | P 14.1% |
| Found | 43.2% | 4.6% | 16.2% | 13.5% |

NMR (δ,ppm) in $CDCl_3$:$CH_2$ with P as multiplet between 2.1 and 2.6. Acetylene proton at 2.69. $CH_2$ with Cl as multiplet between 3.52 and 4.0. Ester-$CH_2$ with O between 4.6 and 4.8 (multiplet).

EXAMPLE 10: Di-(n-butoxycarbonylmethyl) 2-chloroethanephosphonate

To a solution of 13.2 g (0.1 mol) of glycolic acid butylester and 9.1 g (0.05 mol) of chloroethane phosphonic acid dichloride in 100 ml of absolute ether are added with stirring a solution of 7.9 g (0.1 mol) of absolute pyridine in 50 ml of absolute diethyl ether. A white precipitate results and the reaction mixture begins to boil. Stirring is continued for a further 15 hours at 25° and the precipitated hydrochloride is removed by filtration. The ethereal filtrate is extracted with 2 50 ml portions of 2N hydrochloric acid, followed by 2 50 ml portions of 2N sodium hydroxide solution and then washed to neutrality with water, dried and concentrated by evaporation. Further evaporation of the concentrate under high vacuum in a rotary evaporator for 2 hours at 25° results in a colourless oil having the following characterisation data:
$n_D^{20°}$ = 1.4525
Analysis: $C_{14}H_{26}ClO_7P$ Mol weight: 373.8

|  |  |  |  |  |
|---|---|---|---|---|
| Calc. | C 45.1% | H 7.0% | Cl 9.5% | P 8.3% |
| Found | 44.6% | 7.0% | 9.5% | 8.3% |

NMR (δ, ppm) in $CDCl_3$: butyl protons as wide multiplets at 0.8 – 1.8. Butyl-$CH_2$ with O as multiplet at about 4.2. $CH_2$ with P between 2.15 and 2.85 and $CH_2$ with Cl between 3.6 and 4.1 (multiplets). Glycolic acid-$CH_2$ as doublet at 4.68 with $J_{PH}$ = Hz.

EXAMPLE 11: Di-(tetrahydropyran-2-ylmethyl) 2-chloroethanephosphonate

To a solution of 11.6 g (0.1 mol) of 2-hydroxymethyl-tetrahydropyran and 9.1 g (0.05 mol) of 2-chloroethane phosphonic acid dichloride in 200 ml of absolute diethyl ether is added a solution of 7.9 g (0.1 mol) of absolute pyridine in 50 ml of absolute diethyl ether with stirring. During the addition a white precipitate is formed. Stirring is continued for a further 15 hours at 35°,after which the precipitate is removed by filtration and the ethereal filtrate is washed to neutrality with hydrogen carbonate solution, followed by water. The ethereal solution is concentrated by evaporation and further evaporated in high vacuum in a rotary evaporator for 4 hours at 25°, to yield a product with the following characterisation data: $n_D^{20°}$ = 1.4810 Analysis: $C_{14}H_{26}ClO_5P$ Mol weight: 340.9

|  |  |  |  |  |
|---|---|---|---|---|
| Calc. | C 49.3% | H 7.7% | Cl 10.7% | P 9.1% |
| Found | 49.4% | 7.7% | 10.4% | 9.3% |

NMR (δ, ppm) in $CDCl_3$: methylene protons of the tetrahydropyran ring, which are not adjacent to the O, as multiplets between 1.2 and about 2.0. $CH_2$ with P as multiplet at 2.1 – 2.7. Remaining protons as overlapping multiplets between 3.1 and 4.2.

EXAMPLE 12: Di-(3-ethoxycarbonyl-n-propyl) 2-chloroethanephosphonate

To a solution of 13.2 g of ethyl 4-hydroxybutyrate (produced as described in J. Org. Chem. 31, 487 (1966)) and 9.1 g (0.05 mol) of 2-chloroethane phosphonic acid dichloride in 100 ml of absolute diethyl ether is added a solution of 7.9 g (0.1 mol) of absolute pyridine in 50 ml of absolute diethyl ether. During the addition white crystals are precipitated and the temperature increases to 35°. Stirring is continued for a further 20 hours at 40°.

After the reaction mixture has been cooled to room temperature the crystals are removed by filtration and the ethereal filtrate is washed to neutrality with hydrogen carbonate solution followed by water. The ethereal solution is concentrated by evaporation and further evaporated in high vacuum for 24 hours at 25°, resulting in a clear yellow oil with the following characterisation data:
$n_D^{20°}$ = 1.458
Analysis: $C_{14}H_{26}ClO_7P$ Mol weight: 372.8

|  |  |  |  |  |
|---|---|---|---|---|
| Calc. | C 45.1% | H 7.0% | Cl 9.5% | P 8.3% |
| Found | 44.8% | 6.9% | 9.8% | 8.1% |

NMR (δ, ppm) in $CDCl_3$: ester $CH_3$ as triplet at 1.27. The protons of the two $CH_2$ groups which are adjacent to the CO group, as well as the $CH_2$ with P appear as superimposed multiplets between 1.75 and 2.65. $CH_2$ with Cl 3.52 – 3.87. All $CH_2$ with O as superimposed multiplets between 3.96 and 4.48.

What is claimed is:
1. A compound of the formula:

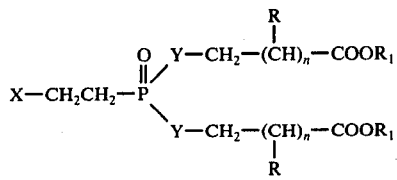

wherein
X is chlorine or bromine,
Y is oxygen or sulfur,
R is hydrogen, $C_1$–$C_6$ alkyl, $C_3$–$C_6$ cycloalkyl, unsubstituted phenyl or phenyl substituted by one or more members selected from the group consisting of fluoro, chloro, bromo, cyano, carboxy, $C_2$–$C_8$ alkoxycarbonyl, $C_2$–$C_8$ alkylcarbamoyl, trihaloalkyl, $C_1$–$C_8$ alkylsulphinyl, unsubstituted phenylsulphinyl, phenylsulphinyl substituted by a methyl or ethyl group or two methyl groups, $C_1$-$C_8$ alkylsulphonyl, unsubstituted phenylsulphonyl, phenylsulphonyl substituted by a methyl or ethyl group or two methyl groups, and nitro, $R_1$ is $C_1$-$C_8$ alkyl, $C_3$-$C_6$ cycloalkyl, unsubstituted phenyl or phenyl substituted by one or more members selected from the group consisting of fluoro, chloro, bromo, cyano, carboxy, $C_2$-$C_8$ alkoxycarbonyl, $C_2$-$C_8$ alkylcarbamoyl, trihaloalkyl, $C_1$-$C_8$ alkylsulphinyl, unsubstituted phenylsulphinyl, phenylsulphinyl substituted by a methyl or ethyl group or two methyl groups, $C_1$-$C_8$ alkylsulphonyl, unsubstituted phenylsulphonyl, phenylsulphonyl substituted by a methyl or ethyl group or two methyl groups, and nitro, and $n$ is 0, 1 or 2.

2. A compound of claim 1 in which $R_1$ is alkyl and $n$ is O.

3. The compound according to claim 2, which is di-(n-butoxycarbonylmethyl) 2-chloroethanephosphonate.

4. A method of regulating the growth of plants or regulating plant secretion by applying to the plants a plant growth or secretion regulating effective amount of a compound according to claim 1.

5. A method according to claim 4, for stimulating latex flow in latex-forming plants by the application to the plants of a latex flow stimulating effective amount of the compound.

6. A method according to claim 5, in which the latex-forming plants are *Hevea brasiliensis*.

7. A method according to claim 5, in which the compound is applied to latex-forming plants in an amount between 0.2 to 0.8 g per tree.

8. A plant growth or plant secretion regulating formulation comprising a plant growth or secretion regulating effective amount of a compound according to claim 1 in association with a plant growth regulator carrier, diluent and/or adjuvant.

9. A formulation according to claim 8, in which the compound dissolved in an organic solvent and sufficient thickening agent to render the formulation of a jelly constituency.

10. A formulation according to claim 9, in which the organic solvent comprises xylene and either dimethyl sulphide or dimethyl formamide, and the thickening agent comprises hydroxyethyl cellulose.

11. The compound according to claim 1 which is di-(ethoxycarbonylethyl) 2-chloroe thanephosphonate.

12. The compound according to claim 1 which is di-(2-ethoxycarbonyl-2-phenylethyl) 2-chloroethanephosphonate.

13. The compound according to claim 1 which is di-(2-ethoxycarbonylethyl) 2-chloroethanedithiophosphonate.

14. The compound according to claim 1 which is di-(3-ethoxycarbonyl-n-propyl) 2-chloroethanephosphonate.

* * * * *